(12) United States Patent
Baumann et al.

(10) Patent No.: US 12,070,185 B2
(45) Date of Patent: Aug. 27, 2024

(54) OBSERVATION DEVICE AND METHOD OF OPERATING AN OBSERVATION DEVICE

(71) Applicant: KARL STORZ SE & Co KG, Tuttlingen (DE)

(72) Inventors: Harald Baumann, Tuttlingen (DE); Benjamin Häsler, Tuttlingen (DE); Marcel Hofstetter, Tuttlingen (DE); Hans-Georg Mathe, Tuttlingen (DE)

(73) Assignee: KARL STORZ SE & CO KG, Tuttlingen (DE)

( * ) Notice: Subject to any disclaimer, the term of this patent is extended or adjusted under 35 U.S.C. 154(b) by 373 days.

(21) Appl. No.: 16/944,704

(22) Filed: Jul. 31, 2020

(65) Prior Publication Data
US 2021/0044754 A1    Feb. 11, 2021

(30) Foreign Application Priority Data
Aug. 8, 2019    (DE) .......................... 102019121434.3

(51) Int. Cl.
*A61B 1/00* (2006.01)
*A61B 1/05* (2006.01)
(Continued)

(52) U.S. Cl.
CPC .... *A61B 1/00096* (2013.01); *A61B 1/000094* (2022.02); *A61B 1/00045* (2013.01);
(Continued)

(58) Field of Classification Search
CPC ........ H04N 5/23296; H04N 2005/2255; A61B 1/00045; A61B 1/00096; A61B 1/00174;
(Continued)

(56) References Cited

U.S. PATENT DOCUMENTS

| 4,902,115 A | 2/1990 | Takahashi |
| 6,734,911 B1 | 5/2004 | Lyons |

(Continued)

FOREIGN PATENT DOCUMENTS

| DE | 102005036486 A1 | 1/2007 |
| JP | 2009080410 A | 4/2009 |

OTHER PUBLICATIONS

Scheffler, A., European Search Report, App 20189448.2-1122, Dec. 8, 2020, pp. 1-7, Munich.
(Continued)

*Primary Examiner* — Lin Ye
*Assistant Examiner* — Chan T Nguyen
(74) *Attorney, Agent, or Firm* — David N. Villalpando (57) ABSTRACT

An observation device and method its operation is disclosed. The device includes an instrument with a shaft having a proximal end and a distal end; objective optics disposed at the shaft and having a field of view; an imaging sensor arranged to capture image data, the imaging sensor having a sensor array of evenly distributed elements; and an image processing unit. The objective optics is arranged to capture a scene in the field of view on the imaging sensor. The objective optics define at least a central imaging region and a peripheral imaging region, where the differing focal lengths of the objective optics result in the central imaging region having a higher digital resolution than that of the peripheral region, resulting in more pixels dedicated to the region of interest, while the peripheral regions have adequate resolution to monitor the introduction of surgical tools and other valuable information.

20 Claims, 7 Drawing Sheets

(51) Int. Cl.
  *H04N 23/50* (2023.01)
  *H04N 23/69* (2023.01)
(52) U.S. Cl.
  CPC ...... *A61B 1/00174* (2013.01); *A61B 1/00188* (2013.01); *A61B 1/05* (2013.01); *H04N 23/69* (2023.01); *H04N 23/555* (2023.01)
(58) Field of Classification Search
  CPC . A61B 1/00188; A61B 1/05; A61B 1/000094; A61B 1/00002–00009; A61B 1/04–055; G02B 23/2438; G02B 23/243; G02B 23/2415; G02B 7/001; G06T 2207/10068
  USPC ...................................................... 348/240.1
  See application file for complete search history.

(56) References Cited

U.S. PATENT DOCUMENTS

| | | | |
|---|---|---|---|
| 6,844,990 B2 | 1/2005 | Artonne et al. | |
| 6,873,358 B1 | 3/2005 | Shimizu | |
| 6,865,028 B2 | 5/2005 | Moustier et al. | |
| 2003/0090586 A1* | 5/2003 | Jan | H04N 17/002 |
| | | | 348/335 |
| 2007/0091196 A1 | 4/2007 | Miyanohara | |
| 2007/0161854 A1* | 7/2007 | Alamaro | A61B 1/0676 |
| | | | 600/109 |
| 2007/0188407 A1* | 8/2007 | Nishi | G02B 25/001 |
| | | | 348/E5.145 |
| 2008/0158226 A1* | 7/2008 | Shimizu | G02B 13/18 |
| | | | 348/308 |
| 2008/0231692 A1* | 9/2008 | Higuchi | H04N 5/2628 |
| | | | 348/E7.085 |
| 2010/0195007 A1 | 8/2010 | Takahashi | |
| 2011/0054348 A1 | 3/2011 | Hendriks et al. | |
| 2011/0169931 A1* | 7/2011 | Pascal | A61B 1/041 |
| | | | 348/E7.085 |
| 2011/0275889 A1* | 11/2011 | Kase | A61B 1/00177 |
| | | | 600/103 |
| 2012/0162486 A1 | 6/2012 | Asakura et al. | |
| 2012/0249725 A1* | 10/2012 | Corcoran | G06T 3/12 |
| | | | 348/36 |
| 2013/0006056 A1 | 1/2013 | Webb et al. | |
| 2016/0015258 A1 | 1/2016 | Levin et al. | |
| 2016/0105606 A1* | 4/2016 | Hikita | H04N 23/56 |
| | | | 348/65 |
| 2017/0078586 A1* | 3/2017 | Suzuki | A61B 1/00 |
| 2020/0380744 A1* | 12/2020 | Valient | G06T 3/047 |

OTHER PUBLICATIONS

Fröning, P., German Search report, Ap. 102019121434.3, Apr. 15, 2020, pp. 1-6, Munich.

* cited by examiner

OBSERVATION DEVICE AND METHOD OF OPERATING AN OBSERVATION DEVICE

CROSS REFERENCE TO RELATED APPLICATIONS

This application claims priority to German Patent Application No. 102019121434.3, filed Aug. 8, 2019, and entitled, "Observation Device and Method of Operating an Observation Device," and is incorporated herein by reference.

FIELD OF THE INVENTION

The present disclosure relates to an observation device, in particular an endoscopic observation system, comprising an instrument having a shaft, objective optics disposed at the shaft and having a field of view, an imaging sensor arranged to capture image data, and an image processing unit.

BACKGROUND OF THE INVENTION

Observation instruments for medical purposes may have a generally large field of view to provide sufficient information even when there is only a relatively small working distance. For instance, when in addition to the observation instrument also other instruments are inserted in the body of the patient, then the instruments are often inserted through the same orifice or adjacent orifices. That is, for instance, when a surgical instrument is inserted while the observation instrument is already in place, then a surgical instrument is in a blind region until the tip of the surgical instrument enters the field of view. It is thus desirable in many cases to provide for a relatively large field of view.

By way of example, the field of view for an endoscope having a rigid shaft may be in a range between 60° and 90°. By way of example, the field of view for an endoscope having a flexible shaft may be in a range between 105° and 160°.

As a general rule, it is desired to minimize the diameter of the shaft of an observation instrument, in particular in cases where the distal end of the shaft is arranged to be inserted in the body. Further, since miniaturized image sensors are available, in certain type of instruments the objective optics and the image sensors are arranged at the distal tip of the shaft. Since in many cases the diameter of the shaft is restricted, it is often hard if not impossible to include optical zooming features there.

As used herein, the distal end of the shaft is the end of the shaft which is generally facing away from the observer, and which faces the observed object. That is, the distal end of the endoscopic shaft used in an endoscopic observation the portion that is inserted in the body. As used herein, the proximal end is the opposite end of the shaft facing away from the observed object and generally facing the observer. The above understanding of distal and proximal is also applicable to further elements described herein.

In observation instruments, there is often a trade-off between the desired field of view and the image resolution in a central region of the field of view necessary. In the central region, significant information for surgical/diagnostic procedures is present, e.g. organs and tissue portions of interest, working heads of additional instruments, etc. However, in a peripheral region of the field of view, information is present which is useful particularly to ensure patient safety, as the surgeon can better keep track of any introduced instruments, however, the peripheral information can also assist with general orientation and navigation.

Meanwhile, high resolution miniaturized imaging sensors (CCD sensors, CMOS sensors, etc.) have become available which may be placed at the distal end of the shafts of observation instruments. Generally, higher resolution sensors provide image data which can be used for digital zooming and panning. Particularly when the resolution provided by the sensor is larger than the resolution provided by the display (monitor, head mounted display, multimedia projector, display device, etc.) then even loss-free digital zooming is possible. In some cases, even digital zooming based on interpolation is acceptable, provided that, despite of the inherent loss, the resulting quality is sufficient.

U.S. Pat. No. 6,844,990 B2, concerned with panoramic/landscape image capturing, proposes to implement aspheric lenses to capture images with non-even resolution. In this way, an expanded image zone and a compressed image zone are provided. Consequently, improvements over standard fisheye lenses shall be provided, for this specific application. For instance, digital enlargement (zooming) may be applied to the expanded image zone without the need of pixel interpolation. A goal is to enable an interactive representation of the captured images on a computer screen, including selective zooming.

A BRIEF DESCRIPTION OF THE INVENTION

In certain embodiments, the present disclosure relates to medical instruments which are arranged for observing the interior of the body, wherein the instrument is inserted through natural or artificial body orifices.

In further embodiments, the present disclosure generally relates to medical observation instruments, which involves also an observation of the body from outside the body. Generally, however, the present disclosure relates to observation instruments having relatively small working distance or object distance.

In view of the foregoing, it is an object of the present disclosure to present an observation device that provides wide angle views of the observed field, while using image sensors having only a limited size. Preferably, digital zooming is possible for at least a main region of interest of the observed field. While it should be noted that, in most practical implementations of the invention, the main region of interest will be the central region, and it will be referred to as such throughout this specification, the selected region should not be considered limited to the literal central region, as, in some embodiments it may be one or more peripheral regions wherein higher resolution images are obtained. Generally, it is desired to provide an observation device having an observation instrument enabling, on the one hand, a wide angle overview of the operation site, including also an observation of any introduced instruments in the wide angle field of view, while, on the other hand, providing sufficient resolution of the central region of the observed field to provide sufficient image details and to permit digital zooming. As a further boundary condition, miniaturized optics and sensors that fit in a small-diameter shaft of the instrument shall be used. A further object is to enhance the area of application for high resolution sensors by selectively exploiting the resolution in the context of wide field observation. Preferably, the objective optics does not require any adjustment (optical zoom) mechanism, at least in certain embodiments.

In a first aspect of the present disclosure an observation device, in particular an endoscopic observation system includes an instrument comprising a shaft having a proximal end and a distal end; objective optics disposed in the distal end of the shaft, the objective optics having a field of view, an imaging sensor arranged to capture image data, the imaging sensor forming a sensor array composed of evenly distributed sensitive elements; and an image processing unit, where the objective optics is arranged to project a scene in the field of view to the imaging sensor, the objective optics defines at least a central imaging region and a peripheral imaging region within the field of view, the objective optics has different focal lengths in the central imaging region and the peripheral imaging region, where in the central imaging region a first optical imaging resolution and in the peripheral imaging region a second optical imaging resolution is provided, the first imaging resolution being larger than the second imaging resolution, and captured images have at least one wide field peripheral image portion and at least one increased resolution central image portion, and where the image processing unit is arranged to apply digital zooming to the central image portion, while preferably maintaining a magnification of the at least one wide field peripheral image portion.

In accordance with the present disclosure, a beneficial trade-off between wide angle imaging and image resolution in central portions of the image is provided. Hence, an imaging sensor may be used that fits in the interior of the shaft of the instrument. Further, the imaging sensor has an even distribution of sensitive elements (pixels) permitting standard technology image sensors to be utilized.

This enables the peripheral image portion to collect image data at acceptable, yet essentially lower resolution, values without risking a loss of information as to inserted instruments and/or general position/orientation information for navigating the observation instrument and other instruments.

Hence, it is possible to use a lower imaging resolution (fewer pixels per angle of the field of view) so that spare pixels can be used for imaging of the central imaging portion which results in a higher imaging resolution there (larger number of pixels per angle of the field of view).

It is thus also possible, at least in certain embodiments, to enable digital zooming without loss or with low-loss in the central portion, since a sufficient imaging resolution is provided. Provided that the imaging resolution in the central portion is greater than the resolution of the display (monitor, head mounted display, etc.), loss-free or nearly loss-free digital zooming is possible. Hence, selective digital zooming or local digital zooming, in terms of the image portions, can be applied to the images. While it is preferred that a magnification of the at least one wide field peripheral image portion is maintained when the central image portion is digitally enlarged (zoomed-in), there may be other operation modes/display modes which so not require that the peripheral image portion magnification is maintained.

Generally, as used herein, an imaging resolution describes the number of sensitive pixels/elements of the imaging sensor per area unit and/or per angular unit. Since in the context of the present disclosure, the size of the field of view (angle of view) is described by respective aperture angles, the imaging resolution is described by pixels/angular unit.

In regard of optical magnification, the objective optics provides at least two different magnifications over the field of view, namely the central portion and the at least one peripheral portion of the image. The objective optics comprises an objective lens or an objective lens unit having multi-focal properties. That is, at least in a first region a first focal length is present and in a second region a second focal length is present. Hence, at least one aspheric lens, or a set of lenses having different focal lengths and forming together a lens unit may be provided. The first region may be associated with the central portion of the image. The second region may be associated with the peripheral portion of the image. One possible lens system compatible with the present invention similar to that disclosed in U.S. Pat. No. 6,844,990 B2.

In certain embodiments, in the first region a basically constant focal length is present. Further, in certain embodiments, in the second region a basically constant focal length is present. However, this shall not be construed to be limiting. There may be at least sub-regions having a non-constant, varying focal length.

Due to the design of the objective optics and the even pattern of the sensor elements on the imaging sensor, as a result the captured image is at least partially stretched or compressed with respect to other portions. Put differently, at least one portion is enlarged or expanded, with respect to the compressed portion(s). Hence, at least in some embodiments, the objective optics and the imaging sensor are configured to provide anamorphic imaging. As used herein, the terms compressed, enlarged, expanded, etc. primarily relate to the imaging resolution (pixels per angular unit), which is different for different segments of the field of view, and not to data compression and similar measures.

Hence, one of the imaging regions is compressed with respect to the other imaging region. In some embodiments, the captured images are at least partially stretched or compressed in width. This is the case for instance when the central image portion is rectangular and is adjoined by two neighboring (left and right) peripheral image portions which are also rectangular.

In other cases, there may be in addition also a top peripheral image portion and a bottom peripheral image portion which may be also based on low resolution imaging, compared to the central image portion.

Further, in other cases, the central image portion may be circular, and the peripheral image portion may be a ring surrounding the central image portion. In such a case, the images are stretched or compressed radially.

In accordance with the above aspect, the given resolution of an imaging sensor having an even distribution (pixel array) is exploited efficiently with relevant central regions having a high resolution and in peripheral regions a lower, but sufficient resolution. That is, in a given set up (shaft diameter), a beneficial trade-off between image resolution, digital zooming capability, and field of view is provided.

One major benefit of the invention is that, as in the main image regions of interest a greater resolution is provided, digital zooming is possible. Further, as different regions of the image are already defined, due to the different optical magnification, the image processing unit is operable to process those regions differently to enhance the scope of functions, for instance to enable digital zooming, but still maintaining wide angle view. Further image enhancement features may also be simplified by the present invention, such as fluorescent imaging (FI) such as ICG and PDD imaging, for example, by the central area collecting white light data, and peripheral areas collecting FI data, with proper illumination and filtration elements incorporated into the optical design.

Further, in certain embodiments a basically constant focal length may be provided in the central region so that distortions in the central regions can be minimized to a large extent, such that, to the extent possible, distortion is reduced to a non-detectable amount.

Generally, the above described principles may be applied to a rectangular composition of the image, that is, the central image portion and the at least one peripheral image portion are each rectangular. Further, the above described principles may also be applied to a circular composition of the image, wherein the central image portion is a central circle and the at least one peripheral image portion forms a circumferential ring that surrounds the central image portion. Hybrid forms between the rectangular composition and the circular composition may be present, involving an oval configuration and/or a nearly rectangular shape provided with convex sides, for instance.

In an exemplary embodiment, in a uniform image display mode, the image processing unit is arranged to process the captured image data by applying digital zooming to the central image portion and/or the at least one peripheral image portion so that the displayed image has uniform magnification properties.

When the captured image based on evenly distributed CCD, CMOS, or other sensors is displayed on a display based on a proportional allocation/mapping between image pixels and display pixels, then the displayed image clearly has a magnified, more detailed representation (central portion having large focal length) and a compressed, reduced-scale representation (peripheral portion having small focal length). That is, in such a case the optical magnification factor is different along the displayed view.

However, the image can be processed so that eventually a compensation of the different optical magnification can be applied resulting in a displayed scene which appears to have uniform image magnification.

For instance, assuming that the peripheral portion is somewhat compressed (that is, fewer pixels per angular unit are assigned to the peripheral portion at the imaging sensor), then the peripheral portion may be up-scaled to meet the image magnification that is already present in the central portion. To this end, for instance, pixel interpolation and similar measures may be used.

In certain embodiments, however, the central portion may be down-scaled to arrive at the image magnification that is already present in the peripheral portion. Needless to say, also a simultaneous processing may be present where the peripheral portion is up-scaled and the central portion is down-scaled to meet at defined magnification factors, any such defined magnification factor may be selected by the user, for example a 1:1 magnification of central region vs. peripheral regions, or, if, for example the central region has 3 times the horizontal resolution of the peripheral regions, the one such magnification factor could be a 3:1 magnification of the central region to the peripheral region.

Hence, in accordance with this aspect, image data is processed before displaying to bring the image into a condition as if it was captured using an objective lens having a constant or basically constant focal length along the entire optical surface of the lens. In other words, in the uniform image display mode, the processing unit compensates for the different focal lengths.

In a further exemplary embodiment, in a first non-uniform image display mode, the image processing unit is arranged to relay the central image portion and the at least one peripheral image portion non-zoomed so that the displayed image has non-uniform magnification properties corresponding to the different focal lengths. The non-zoomed transmission of the image (data) means that the central image portion and the at least one peripheral image portion are not differently treated, in view of digital zooming/compression/stretching. Hence, it may still be possible that a certain digital zooming (e.g., up-scaling, down-scaling) is applied to both the central and the peripheral image portion. However, such measures do not compensate for the different optical magnification due to the different focal lengths. In other words, a digital zoom magnification factor for both regions is the same in this embodiment.

Hence, when there are no compensation measures, the displayed image is partially compressed or stretched so that certain portions of the observed field having the same angular size appear to have a different size on the display. This applies in particular to portions of the peripheral region when compared to portions of the central region. Hence, in the displayed image, the central image portion is more detailed than the peripheral image portion in the first non-uniform image display mode.

In a further exemplary embodiment, in a second non-uniform image display mode, the image processing unit is arranged to process the captured image data by applying digital zooming to the central image portion so that the displayed image has non-uniform magnification properties.

As the imaging resolution in the central portion is greater than in the peripheral portion, the image processing unit is operable to apply digital zooming to the central portion without significant loss. Still, the peripheral portion and the central portion are based on different optical magnification, whereas in addition digital magnification measures are applied to the central portion.

In certain embodiments, the at least one peripheral image portion is maintained in the displayed image. Since upon digital zooming, the central image portion would basically require more display area, it is possible to maintain the peripheral region but to remove parts of the enlarged central portion so that there would be a basically "blind" gap at the transition between the central portion and the peripheral portion.

However, in certain embodiments, provided that the display is large enough, the image processing unit is operable to maintain the displayed field of view entirely by shifting/expanding the peripheral portion to provide sufficient area for the enlarged view of the central portion. In certain embodiments, the outer margin of the image (outer margin of peripheral portion) can be removed. In certain embodiments, the peripheral portion is down-scaled (unidirectional or multidirectional) to provide sufficient room for the central portion.

In further embodiments, the image processing unit is operable to define a sub-portion of the central portion which is to be displayed in an enlarged view, and to apply down-scaling to the remaining part of the central portion which is not to be displayed in the enlarged view. That is, it is possible to present the non-enlarged remaining part of the central portion in a magnification as if it forms part of the peripheral region. In other words, the remaining part of the central portion is "digitally" shifted to the peripheral portion. However, also hybrid forms are conceivable. That is, the remaining part of the central portion which is not to be displayed in an enlarged view is down-scaled to provide sufficient room for the enlarged view, but not matched with the magnification of the peripheral region.

It is to be noted that the terms first display mode and second display mode are merely used for identifying the two modes and not to define an order. That is, in certain embodiments, only the first non-uniform image display mode or only the second non-uniform display mode is used. In certain embodiments, the first and the second non-uniform image display mode are provided.

In a further exemplary embodiment, the imaging sensor has a defined physical resolution that is uniform over the sensitive sensor area. Hence, a basically constant pixel density is present. This may apply in regard of both directions (two dimensional), e.g. height and width.

In one embodiment, the imaging sensor is capable of providing HD resolution (e.g., 1280×720 pixels). In one embodiment, the imaging sensor is capable of providing FullHD resolution (e.g., 1920×1080 pixels). In one embodiment, the imaging sensor is capable of providing 2K resolution (e.g., 2048×1536 pixels). In one embodiment, the imaging sensor is capable of providing 4K resolution (e.g., 4096×3072 pixels) This is not to be understood to be limiting. When the resolution is sufficiently high, then digital zooming is possible without significant loss of information.

In a further exemplary embodiment, the objective optics defines a right peripheral imaging region and a left peripheral imaging region, wherein the central imaging region is arranged between the right peripheral imaging region and the left peripheral imaging region. Needless to say, the imaging sensor is arranged to capture image signals also in the left and right peripheral region.

In a further exemplary embodiment, the objective optics defines a top peripheral imaging region and a bottom peripheral imaging region, wherein the central imaging region is arranged between the top peripheral imaging region and the bottom peripheral imaging region. Needless to say, the imaging sensor is arranged to capture image signals also in the top and bottom peripheral region.

In a further exemplary embodiment, the objective optics defines a circumferential peripheral imaging region, wherein the central imaging region is surrounded by the circumferential peripheral imaging region. Needless to say, the imaging sensor is arranged to capture image signals also in the circumferential peripheral imaging region.

Generally, the imaging region of the sensor and the image portions do not necessarily have to be the same or congruent. Further, the image provided by the objective optics in the imaging plane defined by the sensor surface of the imaging sensor do not necessarily have to be the same as or congruent with the imaging region of the sensor. There may be marginal portions which are not used by the imaging sensor, for instance for imaging quality reasons. Similar, there may also be marginal portions of the sensor surface of the imaging sensor which are not used and thus not present in the captured image.

In a further exemplary embodiment, the shaft is one of a flexible shaft and a rigid shaft. Hence, the instrument may be arranged as one of a flexible shaft endoscope and a rigid shaft endoscope, for instance.

In a further exemplary embodiment, the instrument comprises optical fibers for image transmission. This may be the case when a flexible shaft instrument is used. Image transmitting optical fibers are arranged between the objective optics and the imaging sensor.

In a further exemplary embodiment, the instrument comprises at least one rod lens for image transmission. This may be the case when a rigid shaft instrument is used. Rod lenses are arranged between the objective optics and the imaging sensor.

In a further exemplary embodiment, the objective optics and the imaging sensor are arranged at a distal end of the shaft. Hence, the objective optics and the imaging sensor are arranged at the distal tip of the shaft, or at least close to the distal tip. In such an arrangement, the size of the sensor has to fit to given installation space restrictions.

In a further exemplary embodiment, the imaging sensor is arranged at one of a proximal end of the shaft and an instrument housing arranged proximally of the shaft. Also, in such an arrangement, installation space restrictions for the size of the sensor and, more particularly, the size of the objective optics may be present.

In certain embodiments, the observation instrument does not have optical zoom features. That is, there are no means to actively alter the focal length. Since there are strict restrictions for the diameter of the shaft, there is often insufficient installation space for optical zoom features.

In an exemplary embodiment, the diameter of the shaft, at least at the distal end of the shaft, is less than 20 mm, preferably less than 15 mm, more preferred less than 12 mm, and more preferred less than 10 mm.

In a further exemplary embodiment, the central imaging region covers a narrow angular field having a narrow field view angle, wherein the peripheral imaging region covers a wide angular field having a wide field view angle, and wherein the narrow angular field overlaps a central portion of the wide angular field. As used herein, the narrow field is a sub-portion of the wide field, wherein in the narrow field a larger focal length is present. The peripheral imaging region may have at least a first and a second section at a right and a left side of the image. The right and the left side are defined by the arrangement of the sensor which is typically a rectangular sensor having a certain aspect ratio, and by the orientation of the display used for representation.

In certain embodiments, the peripheral imaging region and also the central imaging region may be arranged symmetrically with respect to an optical axis that is parallel to a shaft axis of the instrument, at least at the distal end of the shaft.

Further, in certain embodiments, the instrument may be provided with side view capability. Hence, the view direction of the objective optics of such an instrument is inclined with respect to the main axis of the shaft. There are instruments having a fixed side view angle of 30°, for instance. Other values involving even a 90° side view feature are possible.

In a further exemplary embodiment, the wide field view angle is at least 60°, preferably at least 90°, more preferably at least 105°, more preferably at least 120°, and more preferably at least 140°. Hence, the wide field angle is for instance +/−30°, preferably +/−45°, more preferably +/−60°, and more preferably +/−70°, with respect to the central optical axis. In certain embodiments, the wide field angle is less than 160°. Hence, in accordance with this embodiment, the objective optics does not involve a fish-eye length or similar lenses which are capable of providing 180° or nearly 180° field of view.

Within the wide angular field, the narrow angular field is present. That is, the narrow field view angle is smaller than the wide field view angle. However, only the portions of the vital field view angle which are not covered by the narrow field view angle are eventually used for forming the peripheral image portion. In a further exemplary embodiment, the narrow field view angle is between 20% and 60% of the wide field view angle, in a further exemplary embodiment between 30% and 50% of the wide field view angle, and in a further exemplary embodiment between 30% and 40% of the wide field view angle.

In a further exemplary embodiment, the instrument has an object distance of less than 20 cm. In a further exemplary embodiment, the instrument is operable at an object distance of between 0.5 cm and 20 cm, and in a further exemplary embodiment between 1.0 and 6.0 cm, and even contact endoscopy. Hence, in accordance with these embodiments, the instrument is configured for endoscopic imaging within a patient's body. The instrument is not configured for large object distances, such as for panoramic photography, landscape photography, architectural photography, etc.

In a further exemplary embodiment, the imaging sensor is a pixel-based imaging sensor, wherein the first optical imaging resolution is at least 150%, in a further exemplary embodiment 200%, and in a further exemplary embodiment 300% of the second optical imaging resolution. Hence, fewer pixels per angular unit are used for imaging with the second imaging resolution than for the first imaging resolution. That is, in the peripheral portion a lower pixel density per viewing angle range than in the central portion is used.

The second, lower optical imaging resolution is used for the peripheral portion. The resulting resolution is still sufficiently high to enable navigation and to provide an overall impression of the observed site. Due to the non-constant pixel density over the observed field of view, there is a greater pixel capacity for the main area of interest, the central portion.

Generally, as used herein, when reference is made to different imaging resolutions, then this may relate to at least one of the width resolution and the height resolution, depending on the design of the objective optics and the imaging sensor. Hence, in certain embodiments, the different resolution is mainly present in the width direction. However, in certain embodiments, different resolutions are present both in the width direction and in the height direction Further, making reference to the circular configuration of the different portions of the image, then different imaging resolutions may be present in the radial direction. Hybrid forms (oval, etc.) are conceivable.

To compensate for the different imaging resolution and thus to ensure steady proportions in the displayed image, if desired in the selected display mode, the image processing unit can be arranged to adapt the image resolution of the processed image.

In a further exemplary embodiment, the image processing unit comprises an interface for transmitting processed images to a pixel-based display device. Generally, the observation device is arranged for an instant (live or nearly live) representation of the observed scene. It is not the main purpose of the observation device to capture and store image data for representation at a later time.

In certain embodiments, the pixel-based display device has an even pixel distribution. Hence, a constant resolution over the display area is provided. As with the imaging sensor, the display device may be arranged for a genuine loss-free representation of HD images, FullHD images, 2K images, or even 4K images. This is not to be understood to be limiting.

In a further exemplary embodiment, the objective optics comprises a transition region between the peripheral imaging region and the central imaging region, wherein the transition region provides for a transition between the focal length in the central imaging region and the focal length in the peripheral imaging region. Hence, there is no abrupt step between the different focal lengths, but a gradual transition. Further, for manufacturing reasons, respective transition regions may be defined at the involved lens(es) of objective optics. In such an embodiment, it is possible to provide a constant or nearly constant focal length (optical magnification) in the central portion, and a different, but also constant or nearly constant focal length (optical magnification) in the peripheral portion.

It is also possible to define a corresponding transition portion also on the level of the image data so that between the central image portion and the peripheral image portion a transition is provided.

In a further exemplary embodiment, the image processing unit is operable to provide for a transition between the peripheral image portion and the central image portion in the processed images. Hence, a transition between low resolution portions of the image and higher resolution portions of the image is possible. This may also involve a transmission between differently stretched/compressed image portions.

In certain embodiments, it is a goal to have the transition portion only barely visible in the displayed images. In other embodiments, the transition portion may be completely blacked out in order to provide minimal optical disturbance to the user.

In certain embodiments, a frame/box or other markers for distinguishing the central image portion from the peripheral imaging region are provided by the image processing unit. Consequently, when a transition portion is clearly present in the displayed image, the frame or marker may also be present to distinguish the transition portion from the other portions of the image. This is also helpful for navigation and for maintaining an overview.

In certain embodiments, the image processing unit is operable to highlight a border and/or a transitional region between the peripheral image portion and the central image portion in the processed images. This may involve visual highlighting in the displayed images.

In a further exemplary embodiment, the instrument is arranged as a medical observation instrument, in particular as an observation instrument for surgical treatments.

In a further aspect of the present disclosure, there is provided a method of operating an observation device, in particular an endoscopic observation system, where an instrument is provided, the instrument including a shaft having a proximal end and a distal end, an objective optics disposed at the shaft and having a field of view, and an imaging sensor arranged to capture image data, the imaging sensor forming a sensor array composed of evenly distributed sensor elements, where the objective optics is arranged to project a scene in the field of view to the imaging sensor, the objective optics defines at least a central imaging region and a peripheral imaging region within the field of view, the objective optics has different focal lengths in the central imaging region and the peripheral imaging region, and where the central imaging region a first optical imaging resolution and in the peripheral imaging region a second optical imaging resolution is provided, the first imaging resolution being larger than the second imaging resolution, and images are captured having at least one wide field peripheral image portion and at least one increased resolution central image portion, and the captured images are processed including digitally zooming the central image portion, while preferably maintaining a magnification of the at least one wide field peripheral image portion.

In certain embodiments, the method is arranged to operate a device that is arranged in accordance with at least one embodiment of the observation device as disclosed herein.

The operating method and the observation device as presented herein may have similar embodiments and refinements.

It is to be understood that the previously mentioned features and the features mentioned in the following may not only be used in a certain combination, but also in other combinations or as isolated features without leaving the spirit and scope of the present disclosure.

A BRIEF DESCRIPTION OF THE DRAWINGS

Further features and advantages of the disclosure are disclosed by the following description of a plurality of exemplary embodiments, with reference to the drawings.

DETAILED DESCRIPTION OF THE INVENTION

Figure 1:
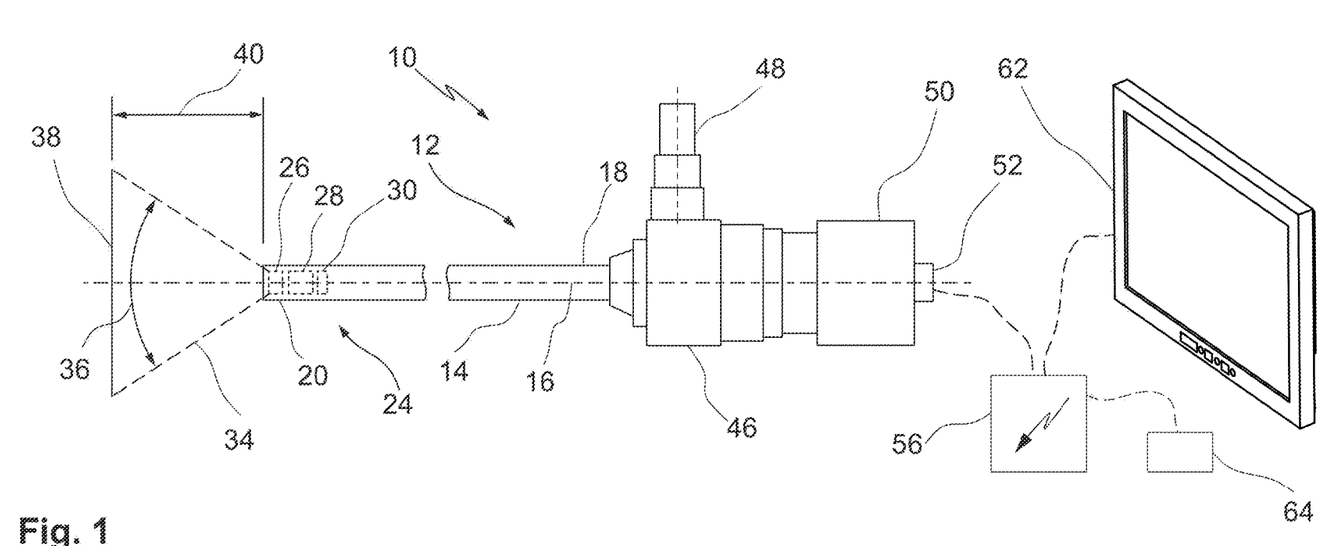
FIG. 1 is a simplified broken side view of an endoscopic rigid shaft observation instrument forming part of an observation device.
Figure 3:
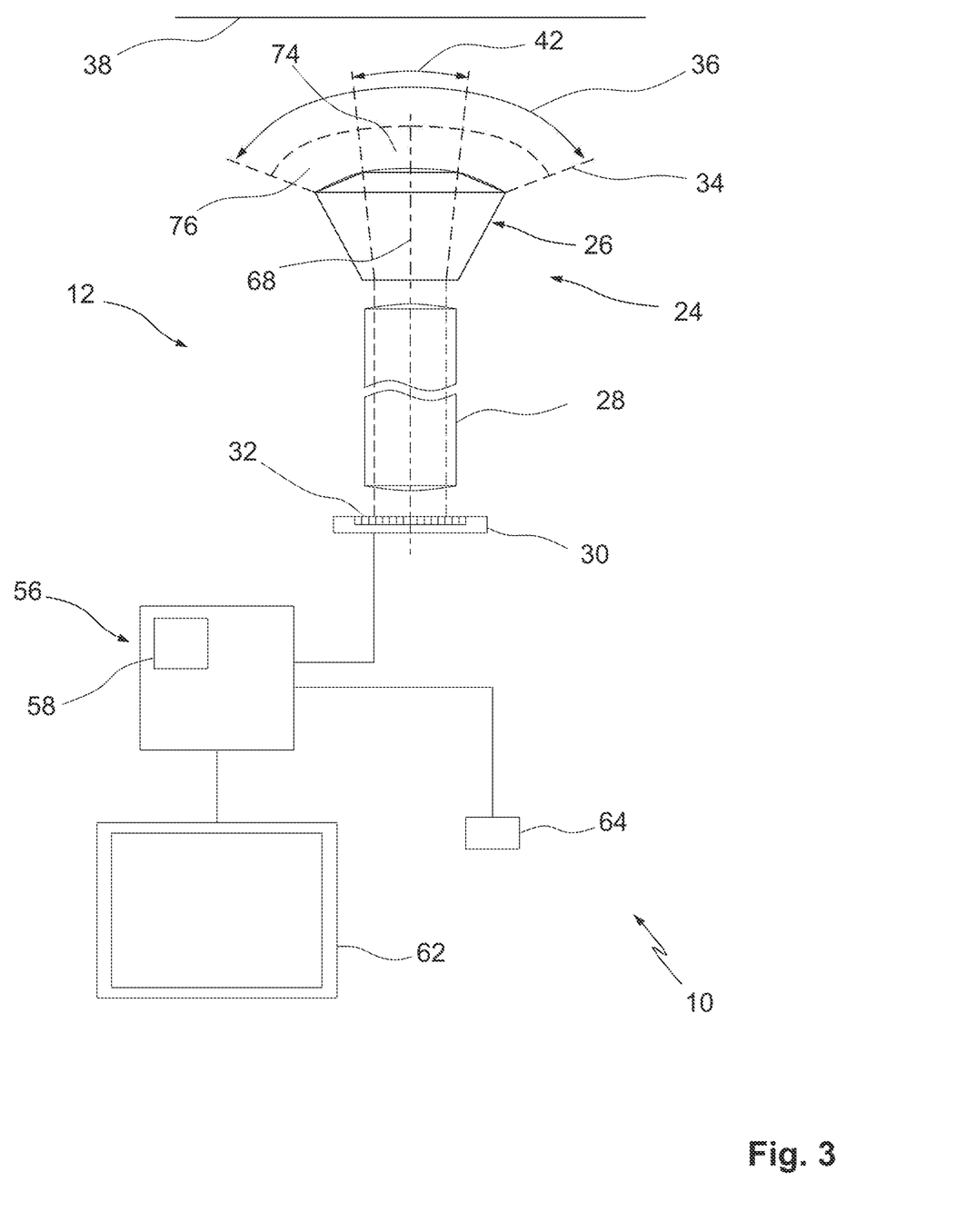
FIG. 3 is a simplified block diagram illustrating an exemplary embodiment of an observation device for multi-focal observation.

With reference to FIG. 1, an exemplary arrangement of an observation device 10, in particular an endoscopic observation system, will be elucidated. Additional reference is made to FIG. 3, illustrating a corresponding schematic simplified block diagram.

The observation device 10 is arranged as a medical observation device for medical procedures, such as surgical procedures, diagnostic procedures, etc. The observation device 10 comprises an instrument 12, in particular an endoscopic instrument. The instrument 12 comprises a shaft 14 having a shaft axis 16. The shaft 14 extends between a proximal end 18 and a distal end 20. At least in certain embodiments, the distal end 20 is inserted into an interior of the body of a patient, through artificial or natural body orifices. However, further applications will be envisaged, wherein the instrument 10 is not necessarily introduced in the body.

At or adjacent to the distal end 20, an optical system 24 is provided. For instance, the optical system 24 comprises an objective optics 26 having at least one objective lens. Further, at least in certain embodiments, an image relay element 28 is provided. The image relay element 28 may be arranged as a rod lens, glass fibers, etc. However, there may be alternative embodiments of the optical system 24 which do not utilize an image relay element 28 so that images are provided and captured as close to the distal end 20 of the shaft 16 as possible. It should also be noted that, while FIG. 1 shows a field of view 34 symmetric about the shaft axis 16, the distal end 20, of the instrument may contain, rather, an optical system angled with respect to the shaft axis 16, resulting in a side- or angle-viewing endoscope, and the elements described herein are equally applicable to those embodiments, all of which are but elements of the present invention.

In the exemplary embodiment of FIG. 1, there is also provided an imaging sensor 30 which is arranged proximally of the optical system 24. Hence, the optical system 24, in particular the objective optics 26, is arranged as imaging optics/projection optics to provide an image of an observed field of view 34 to the imaging sensor 30. The sensor 30 has a photo-sensitive imaging surface 32, see a more detailed illustration in FIG. 3.

In certain embodiments, the instrument 12 is a wide field of view instrument. That is, a view angle 36 is relatively large. For instance, the view angle 36 depicted is between 60° and 160°. Hence, the view angle 36 is at least 60°. In certain embodiments, the view angle 36 is greater than 90°. In certain embodiments, the view angle 36 is greater than 120°. In FIG. 1, the instrument 12 is a so-called rigid shaft instrument. That is, the shaft 16 is not flexible/deflectable. By contrast, reference is made to FIG. 2 which illustrates a similar arrangement of an instrument 212 wherein, however, the instrument 212 is arranged as a flexible shaft instrument. Generally, in a flexible shaft instrument 212 a relatively large view angle may be provided which is, as a general rule, even larger than the view angle of a rigid shaft instrument 12. However, this is not to be understood as limiting.

In FIG. 1, the view direction of the optical system 24 is parallel to the axis 16 of the shaft 14. Hence, also a main axis of the objective lens of the optical system 24 is parallel to or even coincident with the axis 16 of the shaft 14. This is not to be understood to be limiting. There are also instruments known having side view features. In a side view instrument, the main axis of the objective lens of the optical system is inclined with respect to the axis of the shaft, as discussed briefly above.

The instrument 10 is arranged to observe a scene or site 38 at a relatively small working distance or object distance 40. That is, in exemplary embodiments, the working distance 40 is less than 20 cm. For instance, the working distance may be between 1 cm and 6 cm, depending on the actual case of application. In some embodiments, such as those used in contact endoscopy, the object distance 40 can be very small or zero. Since the working distance 40 is relatively small, a wide view angle 36 of the field of view 34 is necessary to provide an overview of the scene. Further, since in many cases further instruments in addition to the observation instrument 10 are used in a medical procedure, which also have to be observed by the observation instrument 10, a large view angle 36 enables overviewing additional instruments which are introduced in the observed scene.

As a general requirement for observation instruments 10, the diameter of the shaft 16 shall be minimized to minimize any exposure on the patient. Hence, in certain embodiments, the shaft diameter of the instrument 10 is less than 15 mm, preferably less than 12 mm, more preferably less than 10 mm. Even smaller diameter values are conceivable in some cases. Hence, there are relatively strict boundary conditions for the installation space for components of the optical system 24 and the imaging sensor 30. However, it should also be noted that there are other applications, envisioned by the present invention, wherein the shaft diameter need not be so small, but is limited, rather, to the necessary size of the optics required to practice the present invention. For example, shaft diameters of greater than 25 mm may also be useful variants of the present invention.

As will be explained further below herein, within the generally large field of view 34 having a wide angle 36, a narrow field having a narrow angle 42 may be defined, see also FIG. 3. In the narrow field, a greater optical magnification is provided by the optical system 24.

In the illustrated embodiment of FIG. 1, the imaging sensor 30 is arranged at or close to the distal end of the shaft 16. This is the case in major embodiments. However, there may be alternative embodiments where the imaging sensor 30 is arranged further proximally, that is, at or close to the proximal end 18 or even further proximally.

In the exemplary embodiment of FIG. 1, the shaft 16 is connected at the proximal end 18 with an instrument's housing 46. In certain embodiments, housing 46 also includes a handling portion where a user can grab and handle the instrument 12. A light connector 48 is connected with the housing 46. In certain embodiments, the light connector 46 forms an interface through which illumination light may be guided to the distal end 18 and eventually to the observed site 38.

At the housing 46 there may be also circuitry provided, refer to a block 50. Circuitry 50 may be provided for controlling the functions of instrument 12. At the distal end of the instrument 12, there is provided an interface 52 through which data are, in particular image data, may be transferred to a control device 56 having an image processing unit 58, see FIG. 3. The control device 56 is coupled with a display unit 62. The display unit 62 may be arranged as a monitor, a head mounted display, etc. Further, for controlling the operation of observation device 10 and for controlling control device 56, control elements 64 for the user may be provided. In exemplary embodiments, control elements 64 may include at least one of a keyboard, a mouse, rotary knobs, switches, speech control, gesture control, etc. Control device 56 may be coupled with any of instrument 12, display 62, and control elements 64 via cables or wireless.

Figure 2:
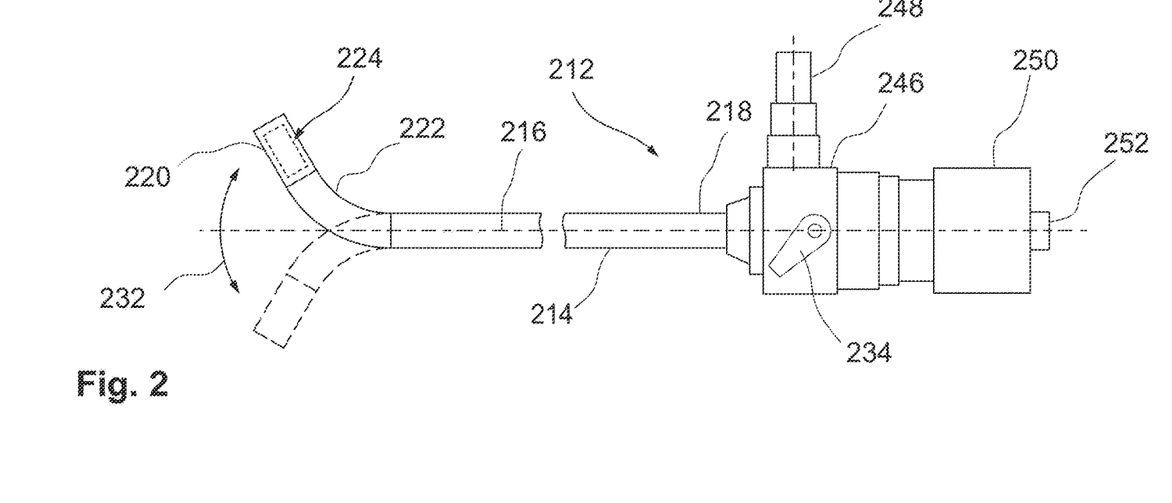
FIG. 2 is a simplified side view of an endoscopic flexible shaft observation instrument.

FIG. 2 illustrates an exemplary embodiment of a flexible shaft observation instrument 212. The instrument 212 has a shaft 214 having a central shaft axis 216. The shaft 214 extends between a proximal end 218 and a distal end 220. At least one portion 222 of the shaft 214 is flexible so that the distal end 220 of the shaft 214 is deflectable. Hence, the instrument 212 has variable side-view capacity. At or adjacent to the distal end, an optical system 224 is provided. Deflection movement of the flexible portion 222 is indicated by a curved double-arrow 232. The user may control the deflection action of the flexible portion 222 via a control mechanism having a control element 234 that is arranged at the instrument's housing 246, for instance.

As with the instrument 12 illustrated in FIG. 1, also the instrument 212 comprises a light connector 248 provided at the housing 212, circuitry 250, and a data interface 252 for transferring image data. Further, as with the instrument 12, also the instrument 212 may be provided with objective objects and an imaging sensor disposed in the shaft 214. Generally, as already discussed hereinbefore, also the instrument 112 may have wide field capacity, wherein the wide view angle may be even greater than the angle 36 illustrated in FIG. 1.

FIG. 3 is a schematic block diagram illustrating an exemplary configuration of an observation device 10 having an instrument 12 as already described in connection with FIG. 1. For illustrative purposes, the shaft and other structural elements of the instrument 12 are not shown in FIG. 3.

The optical system 24 comprises objective optics 26. An image of the observed site 38 is provided by the objective optics 26 and transferred to the sensitive surface 32 of the sensor 30. In the exemplary embodiment of FIG. 3, an image relay element 28 arranged as a rod lens is provided between the objective optics 26 and the imaging sensor 30. However, there are also embodiments which do not require an image relay element 28 since the imaging sensor 30 is arranged even closer to the objective optics 26.

The imaging sensor 30 captures an image and generates image data which is processed in the image processing unit 58 of the control device 56. The images of the observed scene at the site 38 can be displayed via display unit 62. Further, user control elements 64 are provided.

The objective optics 26 is illustrated in the embodiment in FIG. 3 symmetrical with respect to a main axis 68 of the optical system 24. The objective optics 26 comprises at least one objective lens, or a group of objective lenses, providing a multi-focal imaging feature. That is, different portions of the observed side 38 within the relatively large field of view 34 are transmitted to the imaging sensor 30 at different optical magnifications.

By way of example, within the field of view 34 there is provided a central imaging region 74 to which a first focal length is assigned. In addition to the central imaging region 74, two peripheral imaging regions 76 are provided to which a second focal length is assigned. The first focal length is greater than the second focal length. In certain embodiments, the respective focal length within the regions 74, 76 is relatively constant. However, also minor changes of the focal length within the respective region may be acceptable. In any case, there is a significant difference between the general range of the focal length in the central imaging region 74 and the general range of the focal length in the peripheral imaging region 76.

The different optical magnifications for the central imaging region 74 and the peripheral imaging regions 76 applied by the optical system 24 has the effect that a different resolution (pixels per angular unit, for instance) is applied by the imaging sensor 30 when capturing image data. This is the case also with an imaging sensor 30 having a uniform distribution of pixels in the sensitive surface 32.

Figure 4:
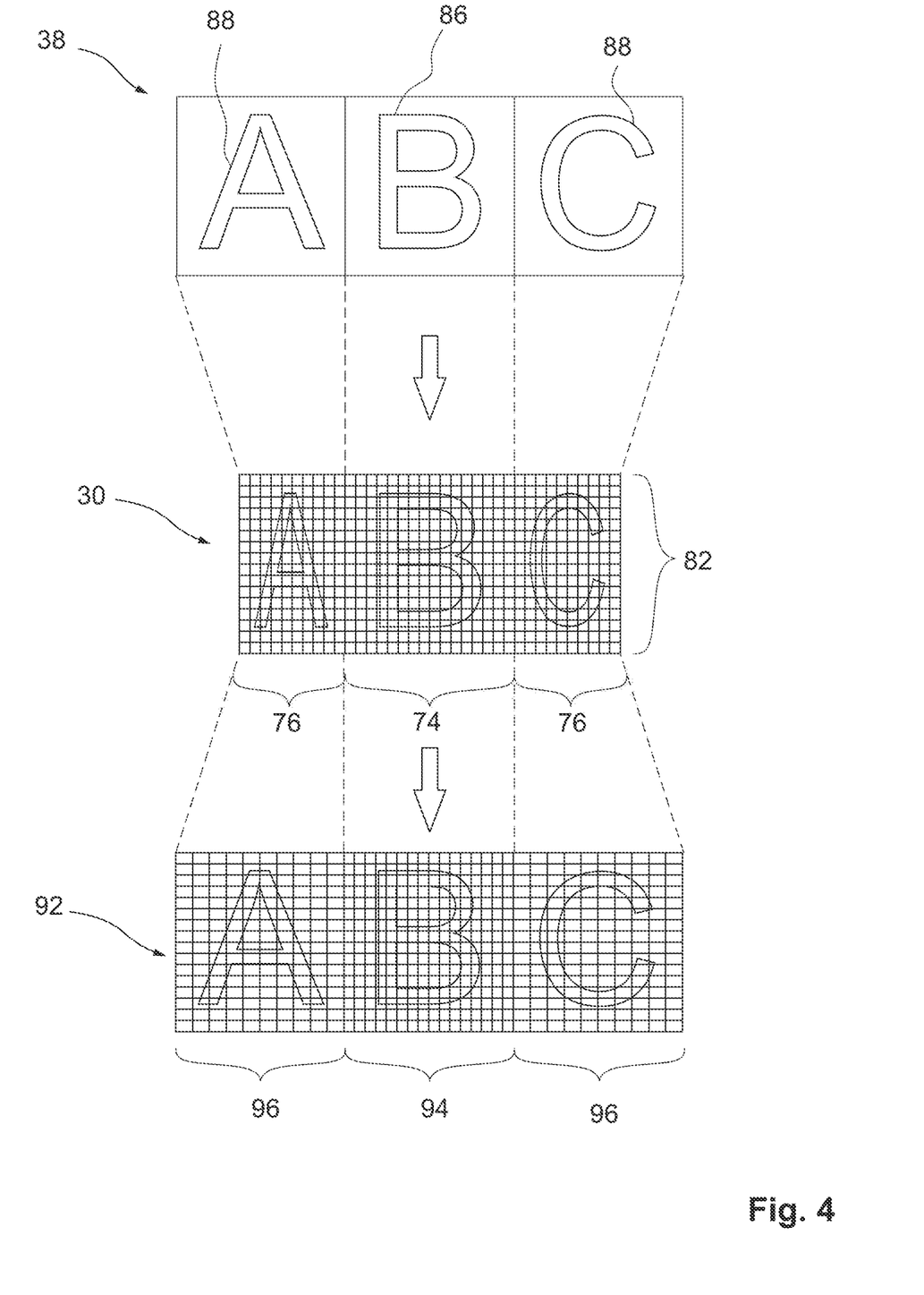
FIG. 4 illustrates an observed wide field image at different levels of the observation and representation.

FIG. 4 is a comparison of illustrations of the observed site 38, where observed objects 86, 88 are present (top portion of FIG. 4), a transmitted image of the observed site 38, as seen by the imaging sensor 30 having a sensor array 82 with an even, fixed pixel distribution (middle portion of FIG. 4), and a resulting resolution in captured image data 92 representing the (restored) image of the observed site 38 (bottom portion of FIG. 4).

The imaging sensor 30 as a constant distribution of sensitive elements (pixels) in the sensor array 82. Hence, the number of pixels per length unit or area unit of the sensitive surface 32 is constant over the extension of surface 32.

In the observed site 38, a central element 86 and peripheral elements 88 are present. A view of the peripheral elements 88 is helpful for general navigation and orientation. However, the main region of interest for the medical procedure is the central element 86. Here, a detailed view is desired.

Due to the multi-focal length characteristics of the objective optics, different optical magnification is applied to different regions 74, 76 of the transmitted image. As can be seen in the middle portion of FIG. 4, the central imaging region 74 has a greater optical magnification than the peripheral imaging regions 76, at least in their width extension.

It is to be noted in this context that in FIG. 4, for illustrative purposes, optical image compression/stretching measures are applied only in the width dimension of the image, as seen by a user. Similar measures may be applied in the height dimension, as will be discussed further below herein.

As shown in FIG. 4, fewer pixels (in the width dimension) are necessary for capturing the peripheral imaging region 76 than for the central imaging region 74. This is caused by the different optical magnifications applied by the optical system 24. Since the sensor 30 has an evenly distributed sensor array 82, the peripheral imaging regions 76 are captured in a compressed state (reduced view) as compared with the central imaging region 74. By contrast, the central imaging region 74 captured by the sender 30 is enlarged with respect to the peripheral imaging regions.

For illustrative purposes, at a bottom portion of FIG. 4, a representation of the captured image data 92 is provided, where a central image portion 94 representing the central imaging region 74 and peripheral image portions 96 representing the peripheral imaging regions 76 are present. To restore the original proportion of the observed objects 86, 88 in the scene at the observed site 38, the peripheral image portions 96 are expanded (up-scaled). Since, however, a different imaging resolution has been applied to the portions 94, 96, the expanded (restored) peripheral image portions 96 have less detailed information than the central image portion 94.

It is to be noted in this context that the bottom portion of FIG. 4 illustrating the non-constant resolution of the image data 92 (relative to their original proportion in the observed site 38) is not necessarily the primary goal for the image display, in terms of the restored proportion. That is, it is in many cases accepted that the peripheral image portions 96 are displayed in a compressed state, since this is sufficient to provide an overview of the large field of view. In return, display area saved in this way is available for a more detailed representation of the central image portion 94.

However, when it is in a uniform image display mode desired to maintain or restore the original proportions of the objects 86, 88 in the observed scene at the site 38, the displayed image may eventually correspond to the bottom portion of FIG. 4 (reference numeral 92), also in terms of proportions of the observed objects 86, 88.

Figure 5:
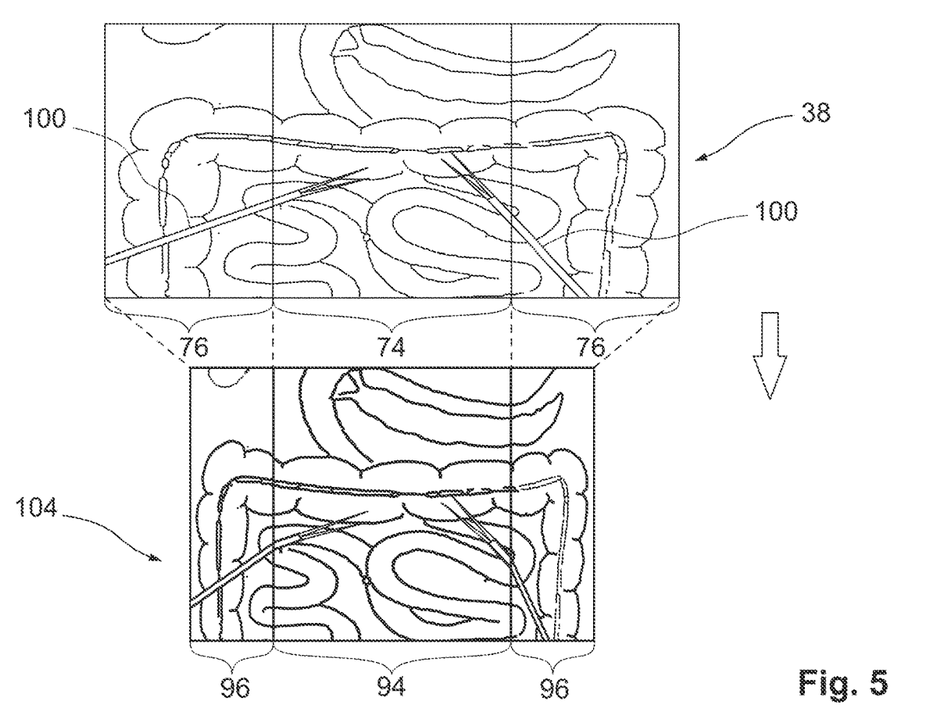
FIG. 5 illustrates an observed wide field image and a resulting display image.

FIG. 5 illustrates a further exemplary arrangement of an observed scene at an observed site 38, whereas the image transmitted by the optical system has a central imaging region 74 and adjacent, peripheral imaging regions 76. In the observed scene, additional instruments 100 are present. The instruments 100 are introduced into the central imaging region 74 via the peripheral imaging regions 76.

Reference numeral 104 illustrates a display mode wherein the central image portion 94 is illustrated in an enlarged state and the peripheral image portions 96 are illustrated in a compressed state. That is, the difference in the optical magnification of the central imaging region 74 and peripheral imaging region 76 is basically maintained in the displayed image. Hence, the display mode 104 may be referred to as non-uniform display mode. Display mode 104 represents a trade-off between large viewing angles and sufficient details in the central image portion 94. Is to be understood that the additional instruments 100 in the peripheral image portions are illustrated in a somewhat distorted state. However, a general overview and also navigating is still possible.

Figure 6:
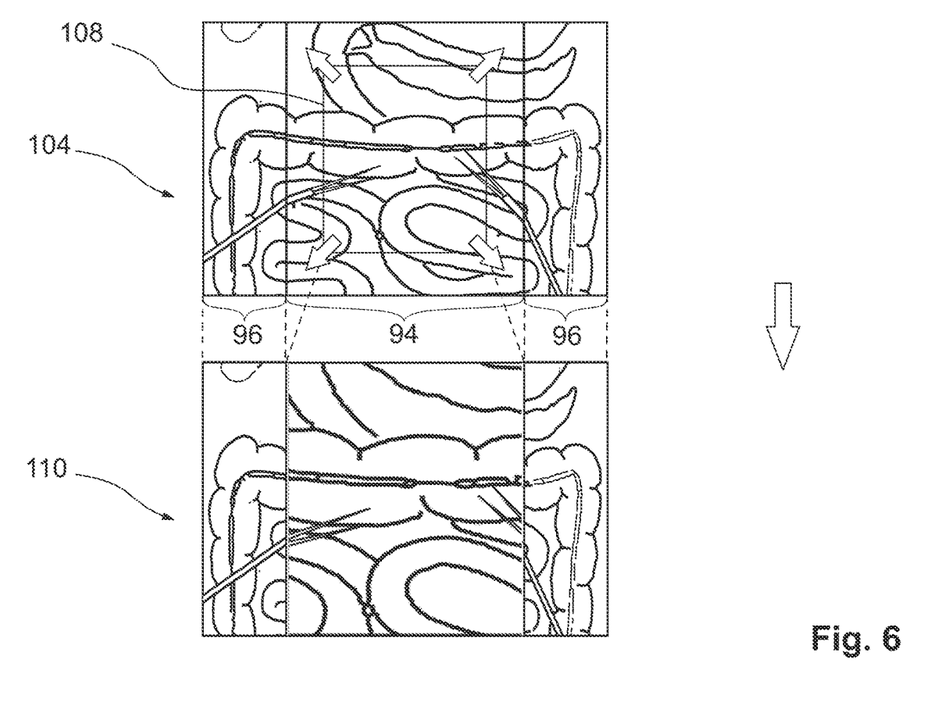
FIG. 6 illustrates digital image processing measures that are applicable to the display image illustrated in FIG. 5.

Based on the display mode 104 already elucidated in FIG. 5, FIG. 6 illustrates an additional display mode 110, wherein the central image portion 94 is partially enlarged. In the top part of FIG. 6, reference numeral 108 indicates a selected enlargement zone in the central image portion 94. The user may select the zone 108 for digital zooming. In the resulting display mode 110, the selected enlargement zone 108 is enlarged and covers basically the entire display area that was previously covered by the central image portion 94.

In the exemplary embodiment illustrated in FIG. 6, the peripheral image portions 96 are maintained and preserved also in the display mode 110. The display mode 110 is a non-uniform display mode as in the displayed image for each of the image portions 94, 96, different magnifications are present, which are attributable to selective optical magnification and selective digital enlargement (digital zooming).

In the exemplary display mode 110, a marginal portion of the central image portion 94 is removed from the displayed image. That is, between the remainder of the central image portion 94 and the peripheral image portions 96, blind portions are present which are not displayed. However, the image information contained in the peripheral image portions 96 is still present so that still an overview of the observed scene is possible.

Figure 7:
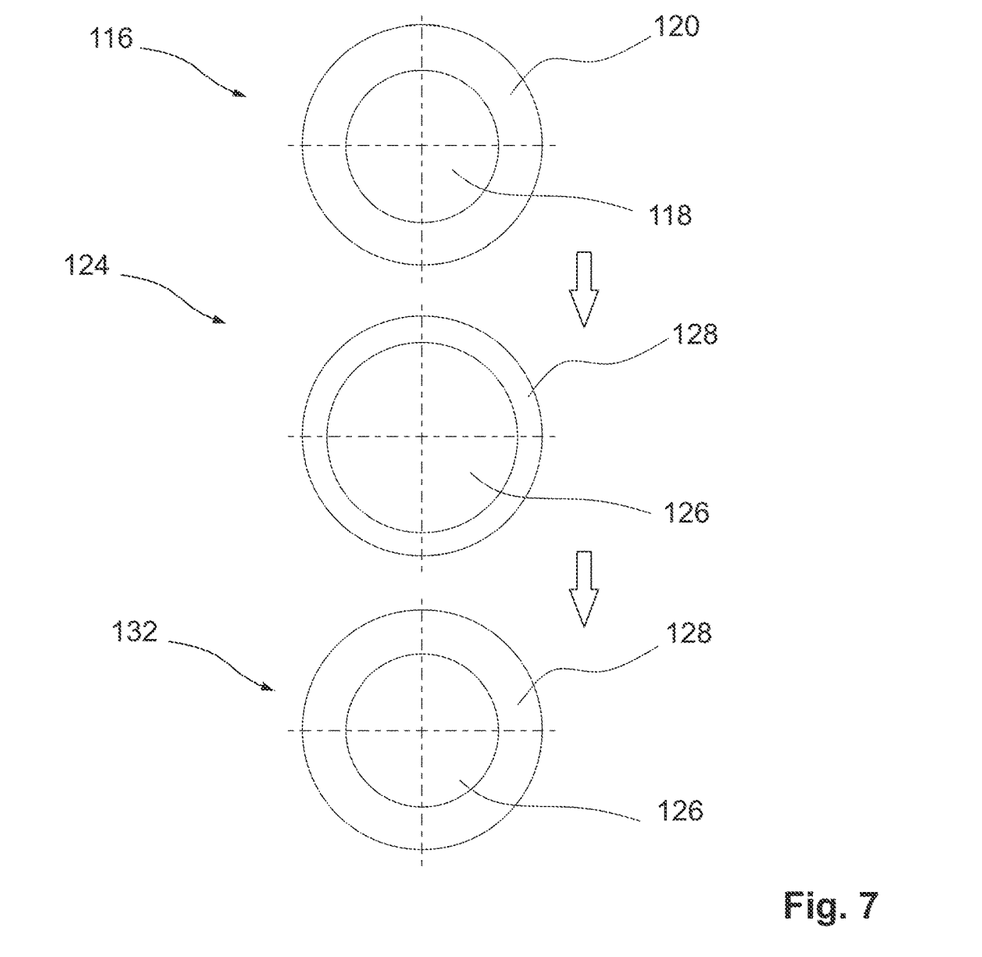
FIG. 7 is a simplified representation illustrating a circular observation field and resulting proportions of imaging regions.

FIG. 7 illustrates that in addition to the rectangular definition of the imaging regions to which different focal lengths are assigned, also circular arrangements may be present. Needless to say, many optical systems are rotationally symmetric with respect to a main optical axis. However, in many cases, the imaging sensor is rectangular so that marginal portions of the image transmitted by the optical system are anyway ignored by the imaging sensor.

In the top portion of FIG. 7, reference numeral 116 designates a circular field of view. In the field of view 116, a circular central imaging region 118 and an annular (ring-shaped) peripheral imaging region 120 are present. As with the foregoing embodiments, the optical system is specifically designed so that in the central imaging region 118 a greater focal length than in the peripheral imaging region 120 is present. Hence, different optical magnifications are applied to the image transmitted by the respective optical system.

In the middle portion of FIG. 7, reference numeral 124 illustrates image data in accordance with the proportion of the image transmitted by an optical system that is based on the circular field of view 116 having a central imaging region 118 and a peripheral imaging region 120. In the image data 124, a central image portion 126 and a peripheral image portion 128 surrounding the central image portion 126 are present. Compared to the proportion of the central imaging region 118 and the peripheral imaging region 120 in the circular field of view 116, the central image portion 126 is enlarged, due to the greater optical magnification, while the image portion 128 is reduced, due to the smaller optical magnification. Hence, fewer pixels per area unit/angular unit are used for the imaging of the peripheral imaging region 120.

In the bottom portion of FIG. 7, reference numeral 132 illustrates a possible display mode in which the central image portion 126 and/or the peripheral image portion 128 are processed so that the displayed image corresponds, in terms of proportion of the central image portion 126 and the peripheral image portion 128 to the original field of view 116. That is, the peripheral image portion may be up-scaled (artificial increase of resolution), whereas the central image portion 126 may be down-scaled (reduction of image resolution). Other display modes than the uniform image display mode 132 are conceivable.

Figure 8:
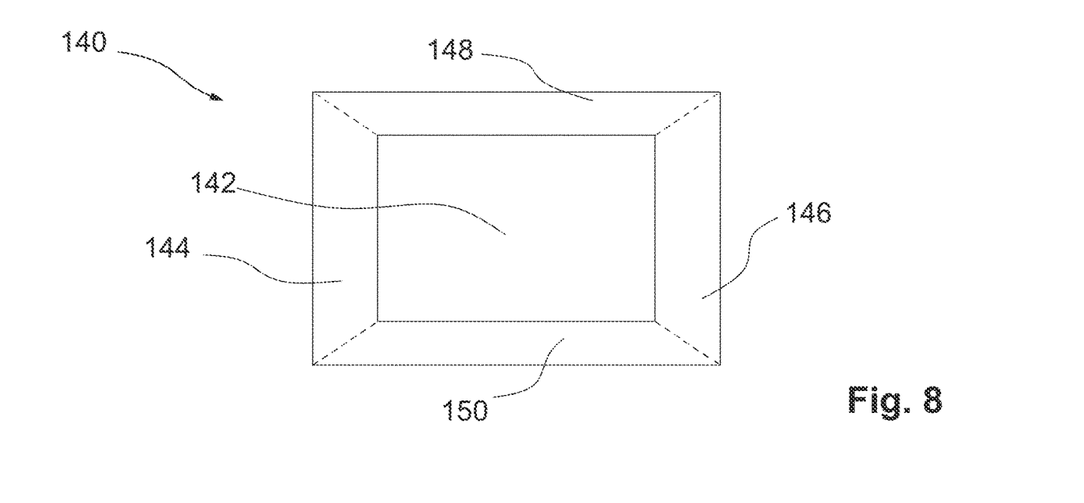
FIG. 8 is a simplified representation illustrating a rectangular observation field that has a surrounding peripheral portion.

FIG. 8 illustrates another exemplary embodiment of a setting of a field of view 140. The field of view 140 is rectangular, whereas a central imaging region 142 having also a rectangular form and peripheral imaging regions 144, 146, 148, 150 are present. That is, the central imaging region 142 is surrounded by peripheral imaging regions 144, 146, 148, 150 also at the top and the bottom side. As with the other embodiments disclosed herein, there may be several display modes in which the image data obtained from the respective zones (having different optical magnification) is selectively processed.

Figure 9:
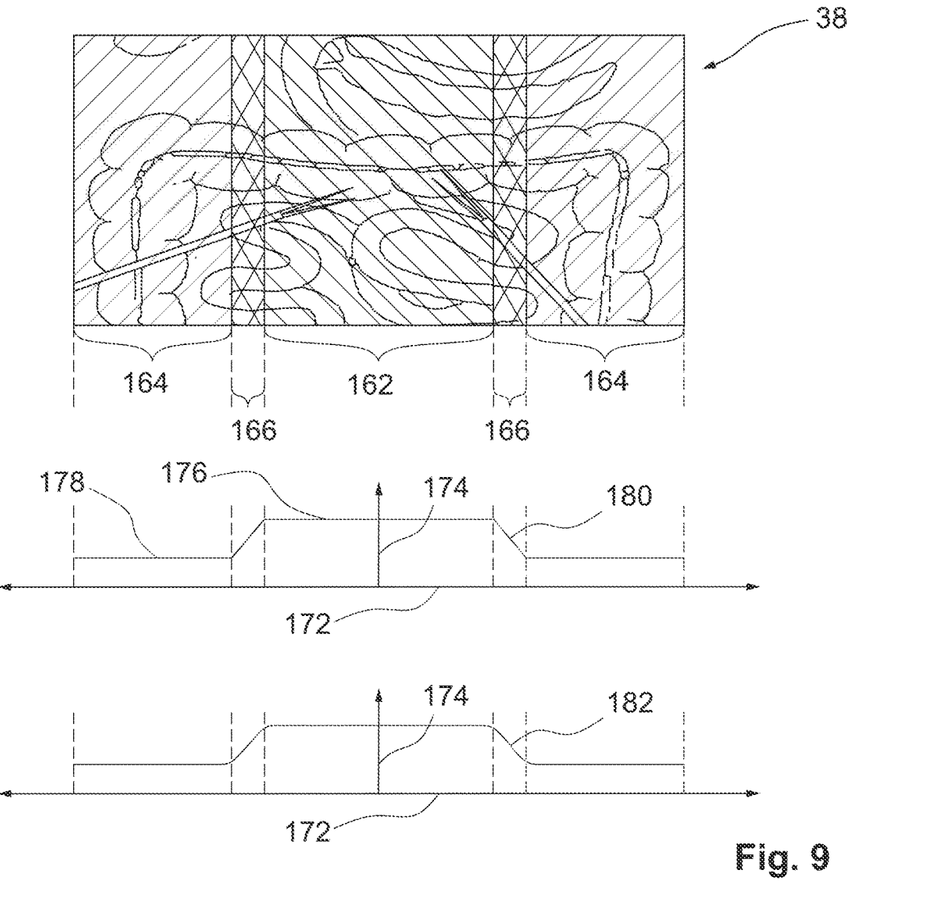
FIG. 9 illustrates an allocation of exemplary focal length characteristics to portions of an observed field, along a width extension of the observed field.

FIG. 9 illustrates exemplary embodiments that utilize not only a central imaging region 162 and peripheral image regions 164, but also a transitional imaging region 166 provided therebetween. In this way, in practice, optical lens design requirements can be simplified. It is generally desired to have a first focal length in the peripheral imaging region 164 and a second focal length in the central imaging region 162. Within each of the two imaging regions 162, 164 the focal length should be basically constant, at least in certain embodiments. However, in practice, there are limits for optical lens designs. For instance, having a first, constant focal length in a first region and a second, constant focal length in a second region would result in a basically unsteady, abrupt transition, provided that it is required that the regions contact one another directly without any intervening region.

In addition, FIG. 9 elucidates two exemplary focal length distributions of the objective optics over the field of view at the observed site. For illustrative purposes, two alternative approaches are illustrated in respective coordinate systems. In each coordinate system, axis 172 designates a respective dimension/extension of the relevant objective lens of the objective optics (e.g. the width extension in the embodiment illustrated in FIG. 9). Axis 174 designates the focal length at a respective (width) position. In the central imaging region 162, a basically constant focal length 176 is provided. In the peripheral imaging region 164, a basically focal length 178 is provided. The focal length 176 is greater than the focal length 178. In the interposed transition imaging region 166, a transition 180 between the different focal lengths 176, 178 is provided. The transition 180 is basically linear so that relatively sharp turns between the three linear sections 176, 178 and 180 are present.

In the alternative exemplary shape of the focal length curve provided in the bottom portion of FIG. 9, a smooth transition 182 between the basically linear focal length portions 176 and 178 is provided. The smooth transition may be arranged to provide a tangential transition between the basically constant but different focal lengths in the central imaging region 162 and the peripheral imaging region 164. Hence, sharp turns can be avoided which may facilitate the design and manufacture of the objective optics.

Figure 10:
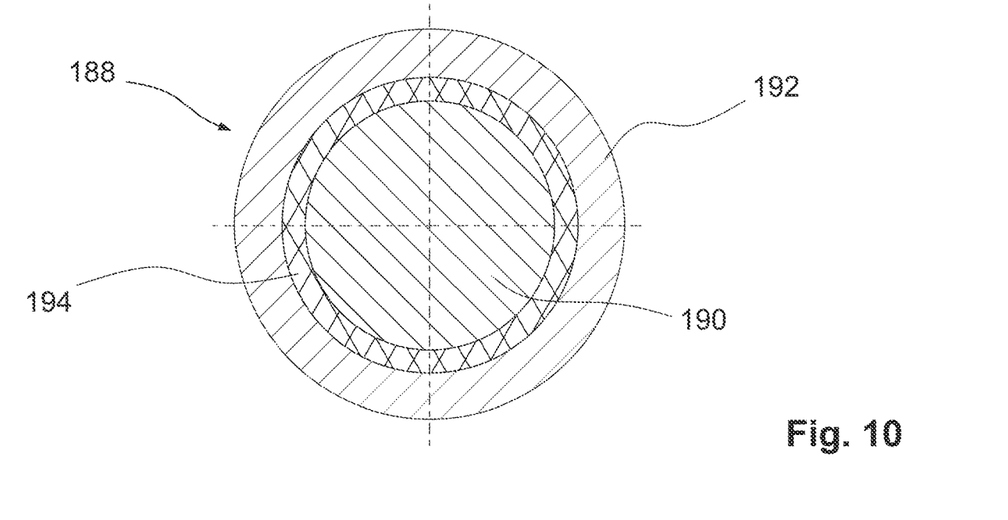
FIG. 10 illustrates a frontal view of an objective optics provided with different focal lengths.

FIG. 10 illustrates a circular field of view 188, refer also the embodiment illustrated in FIG. 7. As with the embodiment of a rectangular field of view in FIG. 9, also for the circular field of view 188, in addition to a central imaging region 190 and a surrounding peripheral imaging region 192, a transition imaging region 194 may be provided. A radial distribution of the respective focal length in the regions 190, 192, 194 may basically correspond to the two exemplary focal length curves (in regard of the width of a rectangular observed site) so that a basically steep, linear transition including sharp turns, or a basically smooth, tangential transition is provided.

Figures 11, 12:
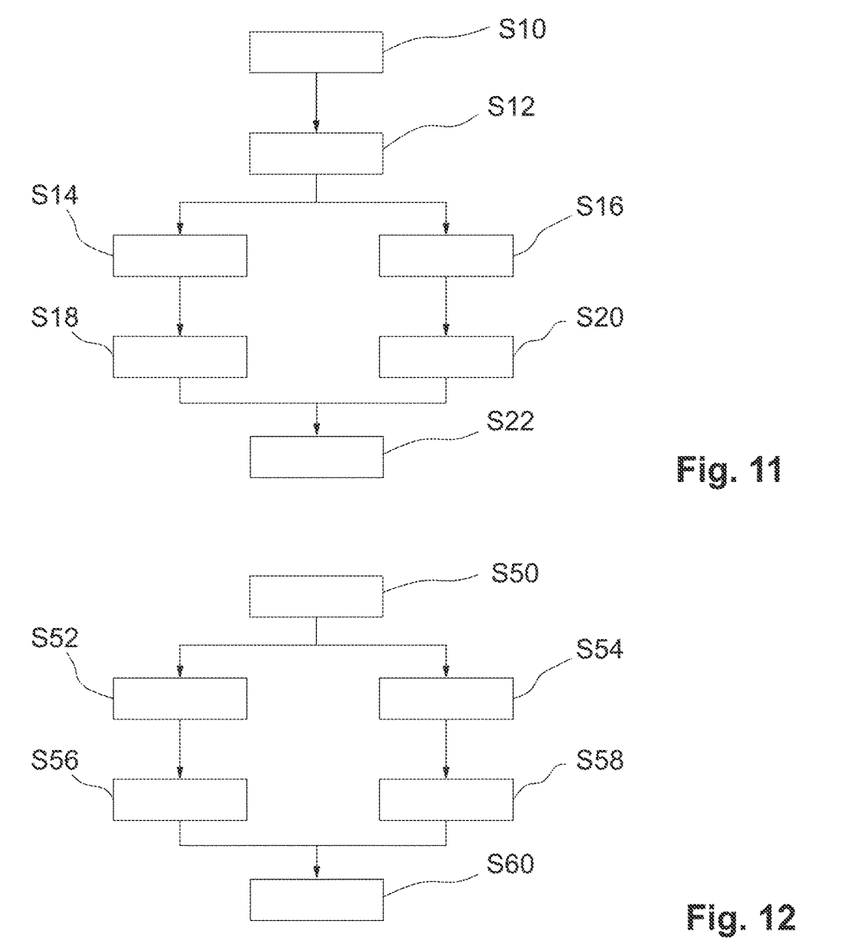
FIG. 11 is a flow chart illustrating an exemplary embodiment of a method for operating an observation device having multi-focal properties.
FIG. 12 is a flowchart illustrating an image processing procedure operable to level out different optical magnifications in the images.

FIG. 11 is a flowchart illustrating an exemplary embodiment of a method of operating an observation device. The method involves a step S10 relating to the provision of an instrument, in particular an endoscopic instrument, which is provided with an objective optics defining a central imaging region and a peripheral imaging region, wherein in the central imaging region and in the peripheral imaging region different focal lengths are provided. The focal length in the central imaging region is greater than the focal length in the peripheral imaging region. The objective optics (optical system) provides an image of the observed scene onto a sensitive area of an imaging sensor. The imaging sensor has a uniform pixel distribution along with the entire sensor surface.

In a further step S12, a scene, for instance a surgical site, is observed with the endoscopic instrument. Since the instrument is preferably provided with wide field capability, a sufficiently large viewing field is possible.

The image provided by the optical system (objective optics) is captured in two parallel steps S14 and S16. Step S14 relates to image acquisition in a central portion, whereas the step S16 relates to image acquisition in a peripheral portion. That is, via an imaging sensor having an evenly distributed sensor array, two distinct portions having different optical magnification may be captured. In other words, due to the design of the imaging sensor and the design of the optical system, the imaging resolution (pixel per angular unit) for the central portion is greater than the peripheral portion.

Subsequent to step S14, a processing step S18 is provided. Step S18 may involve digital zooming (up-scaling, down-scaling), image stretching or image compressing (in one dimension, or in two dimensions), and further measures. Subsequent to step S16, a processing step S20 is provided. Step S20 may involve digital zooming (up-scaling, down-scaling), image stretching or image compressing (in one dimension, or in two dimensions), and further measures. Since both portions have different optical magnification, the processing steps S18 and S20 may have the goal to compensate the optical magnification difference so that the displayed magnification perceived by the user is the same for both portions.

It is to be noted that not in each display mode both the peripheral portion and the central portion are processed. By way of example, the step S18 may also involve isolated digital zooming of the central portion to utilize the increased resolution in this portion. So at least one of the steps S18, S20 may be optional in some operation modes/display modes.

In a further step S22, processed image data representing the central portion and the peripheral portion is combined for simultaneous presentation on a display. Hence, wide field characteristics are maintained so that an overview is possible, whereas in the central portion, the increased resolution may be utilized.

FIG. 12 is a flowchart illustrating data processing measures applied to image data captured by an imaging sensor having evenly distributed pixels that acquires imagers provided through an optical system having non-constant focal lengths.

In a step S50, image data is provided, the image data representing different image portions having different optical magnification which are extracted in steps S52 and S54. More particularly, in the illustrated embodiment, the images have a central portion (step S52) and a peripheral portion (step S54). The optical magnification in the central portion is greater than the optical magnification in the peripheral portion.

Downstream of step S52, in a step S56, digital magnification (zooming-in or zooming-out) may be applied to the central image portion. Downstream of step S54, in a step S58, digital magnification (zooming-in or zooming-out) may be applied to the peripheral image portion.

In at least one display mode (uniform image display mode), at least one of steps S56, S58 digital zooming is applied to level out the differences in optical magnification between the two portions. The data is then combined for display in a step S60. Hence, in the uniform image display mode, it is possible to present a uniform image having a constant resulting magnification, as perceived by the viewer.

Figure 13:
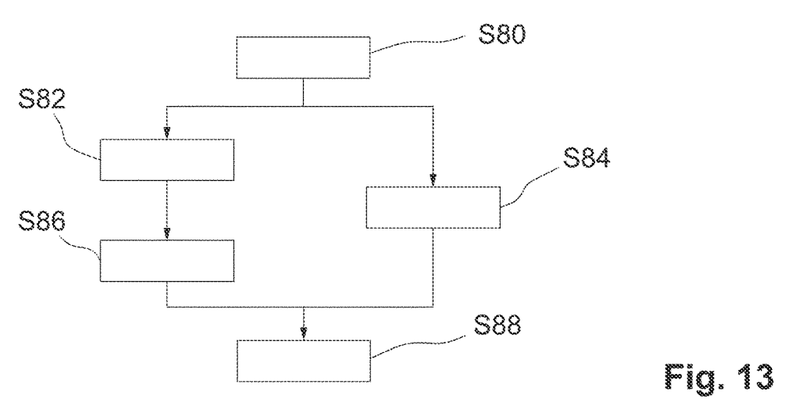
FIG. 13 is a flowchart illustrating an image processing procedure operable to apply digital zooming to portions of a presented image.

FIG. 13 is another flowchart illustrating data processing measures applied to image data captured by an imaging sensor having evenly distributed pixels that acquires imagers provided through an optical system having non-constant focal lengths.

In a step S80, image data is provided, the image data representing different image portions having different optical magnification which are extracted in steps S82 and S84. More particularly, in the illustrated embodiment, the images have a central portion (step S82) and a peripheral portion (step S84).

In the central portion, a greater image resolution than in the peripheral portion is provided. That is, the central portion may be individually enlarged (zoom-in) in a step S86 to provide further details. Digital zooming enlarges the central portion. Since also the peripheral portion is present, a marginal region of the central portion which can no longer be presented in a fixed setting can be removed. This would result in a combined image having a blind gap between the central portion and the peripheral portion. There may be other measures to provide for a transition between the additionally enlarged central portion and the peripheral region.

Consequently, in a step S88 the data representing the two portions is combined for simultaneous display in a non-uniform image display mode.

The invention claimed is:

1. An observation device, in particular an endoscopic observation system, comprising:
    an instrument comprising a shaft having a proximal end and a distal end;
    objective optics disposed at the shaft and having a field of view;
    an imaging sensor arranged to capture image data, the imaging sensor forming a sensor array composed of evenly distributed sensitive elements; and
    an image processing unit,
    wherein the objective optics is arranged to project a scene in the field of view to the imaging sensor;
    wherein the objective optics includes an objective lens configured to capture a single image, the objective lens being symmetrical with respect to a main axis, the single image having a central imaging region and a peripheral imaging region within the field of view, and wherein a focal length of the central imaging region is different than a focal length of the peripheral imaging region, the focal length of the central imaging region generating a first optical imaging resolution and the focal length of the peripheral imaging region generating a second optical imaging resolution, the first imaging resolution being larger than the second imaging resolution; and
    wherein the single image has a peripheral image portion and a central image portion, a resolution of the central image portion being greater than a resolution of the peripheral image portion, and wherein the image processing unit is further configured to expand the peripheral image portion to be a same proportion as the central image portion.

2. The observation device of claim 1 wherein the image processing unit is configured to apply digital zooming to the central image portion, while, preferably, maintaining a magnification of the peripheral image portion.

3. The observation device of claim 2, wherein in a uniform image display mode, the image processing unit is arranged to process the captured image data by applying digital zooming to the central image portion so that the displayed image has uniform magnification properties.

4. The observation device of claim 3 wherein in a first non-uniform image display mode, the image processing unit is arranged to relay the central image portion and the at least one peripheral image portion non-zoomed so that the displayed image has non-uniform magnification properties corresponding to the different focal lengths.

5. The observation device of claim 3 wherein in a second non-uniform image display mode, the image processing unit is arranged to process the captured image data by applying digital zooming to the central image portion so that the displayed image has non-uniform magnification properties.

6. The observation device of claim 1 wherein the imaging sensor has a defined physical resolution that is uniform over the sensitive sensor area.

7. The observation device of claim 1 wherein the objective optics defines a right peripheral imaging region and a left peripheral imaging region, wherein the central imaging region is arranged between the right peripheral imaging region and the left peripheral imaging region.

8. The observation device of claim 1 wherein the objective optics defines a top peripheral imaging region and a bottom peripheral imaging region, wherein the central imaging region is arranged between the top peripheral imaging region and the bottom peripheral imaging region.

9. The observation device of claim 1 wherein the objective optics defines a circumferential peripheral imaging region, wherein the central imaging region is surrounded by the circumferential peripheral imaging region.

10. The observation device of claim 1 wherein the objective optics and the imaging sensor are arranged at a distal end of the shaft.

11. The observation device of claim 1 wherein the central imaging region covers a narrow angular field having a narrow field view angle, wherein the peripheral imaging region covers a wide angular field having a wide field view angle, and wherein the narrow angular field overlaps a central portion of the wide angular field.

12. The observation device of claim 11 wherein the wide field view angle is at least 60°.

13. The observation device of claim 12 wherein the narrow field view angle is between 20% and 60% of the wide field view angle.

14. The observation device of claim 1 wherein the instrument has an object distance of less than 20 cm.

15. The observation device of claim 2 wherein the imaging sensor is a pixel-based imaging sensor, wherein the first optical imaging resolution is at least 150% of the second optical imaging resolution.

16. The observation device of claim 2 wherein the objective optics comprises a transition region between the peripheral imaging region and the central imaging region, and wherein the transition region provides for a transition between the focal length in the central imaging region and the focal length in the peripheral imaging region.

17. The observation device of claim 2 wherein the image processing unit is operable to provide a transition between the peripheral image portion and the central image portion in the processed images.

18. The observation device of claim 17 wherein the image processing unit is operable to highlight a border and/or a transitional region between the peripheral image portion and the central image portion in the processed images.

19. A method of operating an observation device, in particular an endoscopic observation system, comprising the steps of:

providing an instrument comprising a shaft having a proximal end and a distal end; an objective optics disposed the shaft and having a field of view; and an imaging sensor arranged to capture image data, the imaging sensor forming a sensor array composed of evenly distributed sensor elements, wherein the objective optics is arranged to project a scene in the field of view to the imaging sensor;

wherein the objective optics includes an objective lens configured to capture a single image, the objective lens being symmetrical with respect to a main axis, the single image having a central imaging region and a peripheral imaging region within the field of view;

wherein the objective optics has a focal length in the central imaging region and a focal length in the peripheral imaging region that is different than the focal length in the central imaging region, and wherein the focal length of the central imaging region is essentially constant, and the focal length of the peripheral imaging region is essentially constant so as to generate a first optical imaging resolution in the central region and a second optical imaging resolution in the peripheral imaging region, the first imaging resolution being larger than the second imaging resolution;

capturing one or more single images, each single image having a wide field peripheral image portion and a central image portion wherein the central image portion is of higher resolution than the peripheral image portion;

expanding the peripheral image portion to be a same proportion as the central image portion; and processing the one or more captured images.

20. The method of claim 19 wherein the step of processing the captured images further comprises the step of digitally zooming the central image portion, while preferably maintaining a magnification of the at least one wide field peripheral image portion.

* * * * *